(12) United States Patent
Ding et al.

(10) Patent No.: US 11,406,407 B2
(45) Date of Patent: Aug. 9, 2022

(54) VESSEL SEALING WITH FINE DISSECTION FUNCTION

(71) Applicant: Covidien LP, Mansfield, MA (US)

(72) Inventors: Weijiang Ding, Shanghai (CN); Weisheng Lu, Jiangxi (CN); Syed Sarfraz Ahamed, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 87 days.

(21) Appl. No.: 16/926,694

(22) Filed: Jul. 11, 2020

(65) Prior Publication Data

US 2020/0367920 A1 Nov. 26, 2020

Related U.S. Application Data

(63) Continuation of application No. 15/567,411, filed as application No. PCT/CN2015/077336 on Apr. 24, 2015, now Pat. No. 10,758,257.

(51) Int. Cl.
    *A61B 17/28* (2006.01)
    *A61B 17/00* (2006.01)
    (Continued)

(52) U.S. Cl.
    CPC .......... *A61B 17/2816* (2013.01); *A61B 34/30* (2016.02); *A61B 2017/00738* (2013.01);
    (Continued)

(58) Field of Classification Search
    CPC ............ A61B 18/1442; A61B 18/1445; A61B 18/1447; A61B 2018/1442;
    (Continued)

(56) References Cited

U.S. PATENT DOCUMENTS

D249,549 S  9/1978 Pike
D263,020 S  2/1982 Rau, III
(Continued)

FOREIGN PATENT DOCUMENTS

CN  201299462 Y  9/2009
CN  104302239 A  1/2015
(Continued)

OTHER PUBLICATIONS

Chinese Office Action issued in corresponding Chinese Application No. 201610258270.1 dated Nov. 18, 2020, 6 pages.
(Continued)

*Primary Examiner* — Linda C Dvorak
*Assistant Examiner* — Annabeth E Rodriguez
(74) *Attorney, Agent, or Firm* — Carter, DeLuca & Farrell LLP

(57) ABSTRACT

An electrosurgical forceps includes a first elongated shaft member including a first handle member and a first jaw member having a first tissue contacting surface, and a second elongated shaft member including a second handle member and a second jaw member having a second tissue contacting surface. At least one of the first and second handle members is movable relative to the other between an open position, a first approximated position where the first and second tissue contacting surfaces are diametrically opposed to one another, and a second approximated position where the first and second tissue contacting surfaces are laterally offset from one another. A handle connector assembly is selectively engageable with the second handle member and is configured to selectively communicate electrosurgical energy between the first and second tissue contacting surfaces when the first and second handle members are disposed in the first approximated position.

16 Claims, 14 Drawing Sheets

(51) Int. Cl.
*A61B 17/29* (2006.01)
*A61B 18/00* (2006.01)
*A61B 18/14* (2006.01)
*A61B 34/30* (2016.01)

(52) U.S. Cl.
CPC ............... *A61B 2017/2945* (2013.01); *A61B 2018/0063* (2013.01); *A61B 2018/00178* (2013.01); *A61B 2018/00922* (2013.01); *A61B 2018/1432* (2013.01)

(58) Field of Classification Search
CPC ...... A61B 2018/143; A61B 2018/1452; A61B 2018/1455; A61B 2018/1457; A61B 2018/146; A61B 2018/1462; A61B 17/28; A61B 17/2804; A61B 17/2812; A61B 17/2816; A61B 17/282; A61B 17/2833; A61B 17/2841; A61B 17/285; A61B 17/29; A61B 2017/2808; A61B 2017/2825; A61B 2017/2829; A61B 2017/2837; A61B 2017/2845; A61B 2017/2901–2948; A61B 2017/295; A61B 2017/30; A61B 2017/301–308
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,507,774 A | 4/1996 | Holmes et al. |
| D384,413 S | 9/1997 | Zlock et al. |
| 5,746,740 A * | 5/1998 | Nicholas ............ A61B 10/06 606/205 |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 10,758,257 B2 | 9/2020 | Ding et al. |
| 2007/0043352 A1 | 2/2007 | Garrison et al. |
| 2007/0078456 A1 | 4/2007 | Dumbauld et al. |
| 2013/0296843 A1 | 11/2013 | Boudreaux et al. |
| 2014/0214019 A1* | 7/2014 | Baxter, III ......... A61B 17/3201 606/33 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276786 A1* | 9/2014 | Batchelor ........ A61B 18/1442 606/41 |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1* | 3/2015 | Hart ................. A61B 34/76 606/46 |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | |
|---|---|---|
| CN | 205885518 U | 1/2017 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |

(56) References Cited

FOREIGN PATENT DOCUMENTS

| | | |
|---|---|---|
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 A | 5/1986 |
| JP | 1024051 A | 1/1989 |
| JP | 1147150 A | 6/1989 |
| JP | 55106 | 1/1993 |
| JP | 0540112 | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | 07265328 | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2001003400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003, 15 pages.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Issue"; MICCAI 2005 LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler (abandoned).
U.S. Appl. No. 09/177,950, filed Nov. 23, 1998; inventor: Randel A. Frazier, abandoned.
U.S. Appl. No. 09/387,883; filed Sep. 1, 1999; inventor: Dale F. Schmaltz (abandoned).
U.S. Appl. No. 09/591,328, filed Jun. 9, 2000; inventor: Thomas P. Ryan (abandoned).
U.S. Appl. No. 12/336,970; filed Dec. 17, 2008; inventor: Paul R. Sremeich (abandoned).
U.S. Appl. No. 14/065,644, filed Oct. 29, 2013; inventor: Reschke (abandoned).
Heniford et al. "Initial Research and Clinical Results with an Electrothermal Bipolar Vessel Sealer" Oct. 1999.
Chinese Office Action for Application No. 201610258270.1 dated Mar. 27, 2020 with English Translation.

* cited by examiner

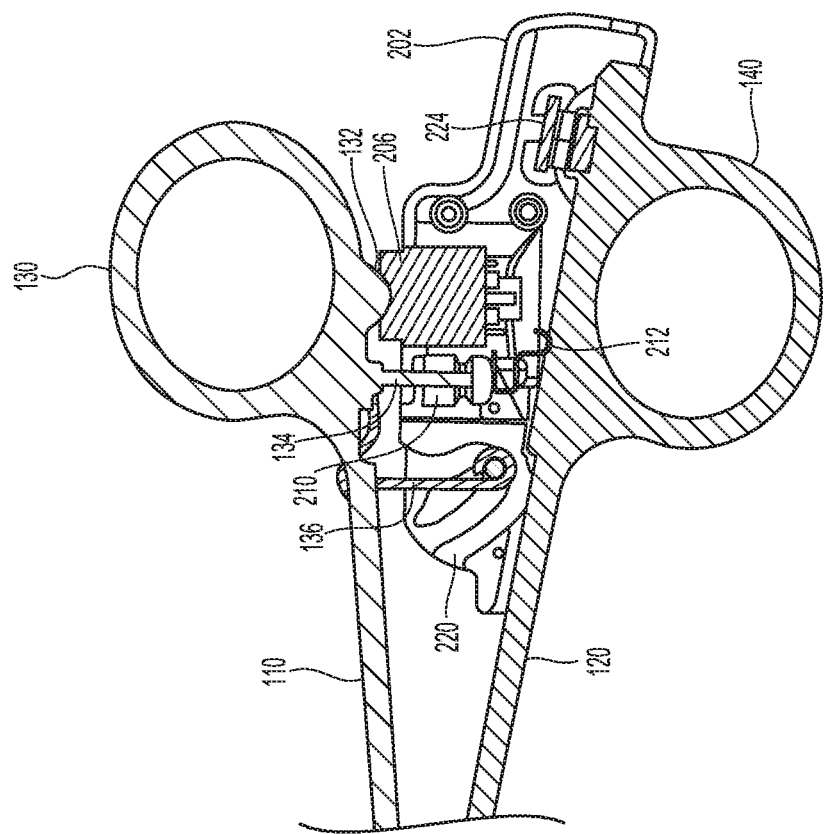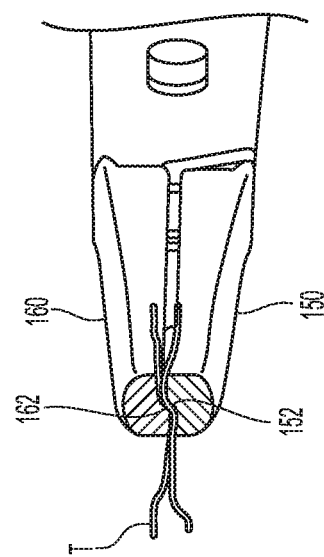
Fig. 14

VESSEL SEALING WITH FINE DISSECTION FUNCTION

CROSS REFERENCE TO RELATED APPLICATION

The present application is a continuation of U.S. patent application Ser. No. 15/567,411, filed Oct. 18, 2017, which is a U.S. National Stage Application under 35 U.S.C. § 371(a) of PCT/CN2015/077336, filed Apr. 24, 2015, the entire contents of each of which are incorporated by reference herein.

BACKGROUND

1. Background of Related Art

The present disclosure relates to energy-based surgical instruments and, more particularly, to energy-based surgical forceps configured for treating and/or cutting tissue.

2. Technical Field

A forceps or hemostat is a plier-like instrument which relies on mechanical action between its jaws to grasp, clamp, and constrict tissue. Energy-based forceps utilize both mechanical clamping action and energy, e.g., electrosurgical energy, ultrasonic energy, light energy, microwave energy, heat, etc., to affect hemostasis by heating tissue to coagulate and/or cauterize tissue. Certain surgical procedures require more than simply cauterizing tissue and rely on the unique combination of clamping pressure, precise energy control, and gap distance (i.e., distance between opposing jaws when closed about tissue) to "seal" tissue. Typically, once tissue is sealed, the surgeon has to accurately sever the tissue along the newly formed tissue seal. Accordingly, many tissue sealing instruments have been designed to incorporate a blade that is movable with respect to a blade slot disposed in a jaw of the tissue sealing instrument to sever the tissue after forming a tissue seal.

Tissue sealing instruments that include a blade and blade slot, however, are typically single-use devices as the blade and blade slot may be difficult to clean, and the blade may wear and dull with repeated use. The incorporation of a blade slot into a jaw of a tissue sealing instrument may reduce the sealing strength of the jaw, and the width of the blade slot may increase the width of the jaw which, in turn, may result in a reduction in the dissection capabilities of the tissue sealing instrument.

SUMMARY

The present disclosure is directed to reusable energy-based surgical instruments having movable, opposed jaw members that are configured for fine dissection, sealing, and/or cutting without the use of a blade and slot jaw configuration.

In accordance with aspects of the present disclosure, an electrosurgical forceps includes a first elongated shaft member including a proximal end portion having a first handle member and a distal end portion including a first jaw member having a first tissue contacting surface, and a second elongated shaft member including a proximal end having a second handle member and a distal end portion including a second jaw member having a second tissue contacting surface. At least one of the first and second handle members is movable relative to the other between an open position, a first approximated position where the first and second tissue contacting surfaces are diametrically opposed to one other, and a second approximated position where the first and second tissue contacting surfaces are laterally offset from one other. A handle connector assembly includes a housing selectively engageable with an inner surface of the second handle member. The handle connector assembly is configured to communicate electrosurgical energy between the first and second tissue contacting surfaces when the first and second handle members are in disposed the first approximated position.

In some embodiments, the first handle member includes a bump stopper disposed on an inner surface of the first handle member that extends towards the second handle member. The bump stopper is spaced from the handle connector assembly when the first and second handle members are disposed in the open position. The bump stopper is configured to engage a switch disposed on the housing of the handle connector assembly when the first and second handle members are moved to the first approximated position.

In some embodiments, the first handle member includes a connector pin extending towards the second handle member. The connector pin is spaced from the handle connector assembly when the first and second handle members are disposed in the open position. The connector pin is configured to extend through a proximal portion of an opening defined in the housing and into contact with a movable first connector member disposed within the housing to close an electrical circuit when the first and second handle members are moved to the first approximated position. In certain embodiments, the connector pin is disposed in an intermediate portion of the opening in the housing, which is distal to, and laterally offset from, the proximal portion of the opening, when the first and second handle members are moved to the second approximated position.

In some embodiments, the first handle member includes a spring connector extending towards the second handle member. The spring connector is spaced from the handle connector assembly when the first and second handle members are disposed in the open position. The spring connector is configured to extend through an opening defined in the housing and into a proximal portion of a channel disposed within the housing when the first and second handle members are moved to the first approximated position. In certain embodiments, the spring connector is disposed within a distal portion of the channel disposed within the housing of the handle connector assembly when the first and second handle members are moved to the second approximated position.

In some embodiments, the first shaft member includes a body portion including a pivot pin and the second shaft member includes a split body portion including first and second legs defining opposed oblong openings. The body portion of the first shaft member is disposed within a slot defined between the first and second legs of the split body portion and the pivot pin extends into the oblong openings. In certain embodiments, when the first and second handle members are in the first approximated position, the pivot pin is disposed in a proximal portion of the oblong openings. In some embodiments, when the first and second handle members are in the second approximated position, the pivot pin is disposed in a distal portion of the oblong openings.

In some embodiments, the first and second tissue contacting surfaces define complementary stepped surfaces. In some embodiments, the first and second tissue contacting surfaces each include a base surface laterally disposed relative to a raised surface. The base and raised surfaces are connected by an intermediate wall that forms a shear edge at an intersection with the raised surface. In certain embodiments, when the first and second handle members are in the first approximated position, the base and raised surfaces of the first tissue contacting surface are aligned with the raised and base surfaces of the second tissue contacting surface, respectively, and when the first and second handle members are in the second approximated position, the raised surfaces of the first and second tissue contacting surfaces are aligned with each other.

In accordance with aspects of the present disclosure, a surgical forceps includes an end effector including first and second jaw members. The first jaw member has a first tissue contacting surface and the second jaw member has a second tissue contacting surface. At least one of the first and second tissue contacting surfaces is configured to communicate electrosurgical energy between the first and second tissue contacting surfaces of the first and second jaw members. Each of the first and second tissue contacting surfaces includes a base surface laterally disposed relative to a raised surface and connected by an intermediate wall. The raised surface and the intermediate wall define a shear edge at an intersection thereof. At least one of the first and second jaw members is movable relative to the other between an open position, a first approximated sealing position, and a second approximated cutting position.

In some embodiments, when the first and second jaw members are disposed in the first approximated sealing position, the base and raised surfaces of the first tissue contacting surface align with the raised and base surfaces of the second tissue contacting surface, respectively. In some embodiments, when the first and second jaw members are disposed in the second approximated cutting position, the raised surfaces of the first and second tissue contacting surfaces align with each other.

In some embodiments, the base and raised surfaces of the first and second tissue contacting surfaces are disposed on curved distal portions of the first and second jaw members. In certain embodiments, distalmost ends of the first and second jaw members include complementary guide surfaces.

In some embodiments, the first jaw member is disposed on a distal end portion of a first shaft member and the second jaw member is disposed on a distal end portion of a second shaft member. The first shaft member includes a body portion extending through a split body portion of the second shaft member such that the first shaft member is centrally aligned with respect to the second shaft member. In some embodiments, the split body portion of the second shaft member defines opposed oblong openings and the body portion of the first shaft member includes a pivot pin that extends into, and is longitudinally translatable and pivotable within, the oblong openings of the second shaft member. In certain embodiments, the split body portion of the second shaft member includes a removable plate.

In some embodiments, the body portion of the first shaft member includes a v-shaped recess and the split body portion of the second shaft member includes a protrusion extending into the v-shaped recess of the first shaft member. When the first and second jaw members are disposed in the open position, the protrusion is disposed in a lower portion of the v-shaped recess to limit longitudinal movement of the first and second shaft members relative to each other. When the first and second jaw members are disposed in an approximated position, the protrusion is disposed in an upper portion of the v-shaped recess and is free to translate within the v-shaped recess.

In accordance with aspects of the present disclosure, a method of treating tissue includes: pivoting at least one of first and second jaw members of an electrosurgical forceps along a first axis to effect movement of the first and second jaw members from an open position to a first approximated position, the first and second jaw members including first and second tissue contacting surfaces, respectively, each of the first and second tissue contacting surfaces including a base surface laterally disposed relative to a raised surface and connected by an intermediate wall, the raised surface and the intermediate wall defining a shear edge at an intersection thereof, wherein the base and raised surfaces of the first tissue contacting surface align with the raised and base surfaces of the second tissue contacting surface, respectively, to grasp tissue therebetween in the first approximated position; applying electrosurgical energy to the tissue grasped between the first and second tissue contacting surfaces of the first and second jaw members to seal the tissue grasped therebetween; and pivoting at least one of the first and second jaw members along a second axis to effect movement of the first and second jaw members from the first approximated position to a second approximated position in which the raised surfaces of the first and second tissue contacting surfaces align to cut the tissue grasped therebetween via the shear edges.

Other aspects, features, and advantages will be apparent from the description, drawings, and the claims.

BRIEF DESCRIPTION OF THE DRAWINGS

FIG. 14 is a side, perspective view, in partial cross-section, of the forceps of FIG. 3;

Corresponding reference characters indicate corresponding parts throughout the drawings.

DETAILED DESCRIPTION

Figure 1:
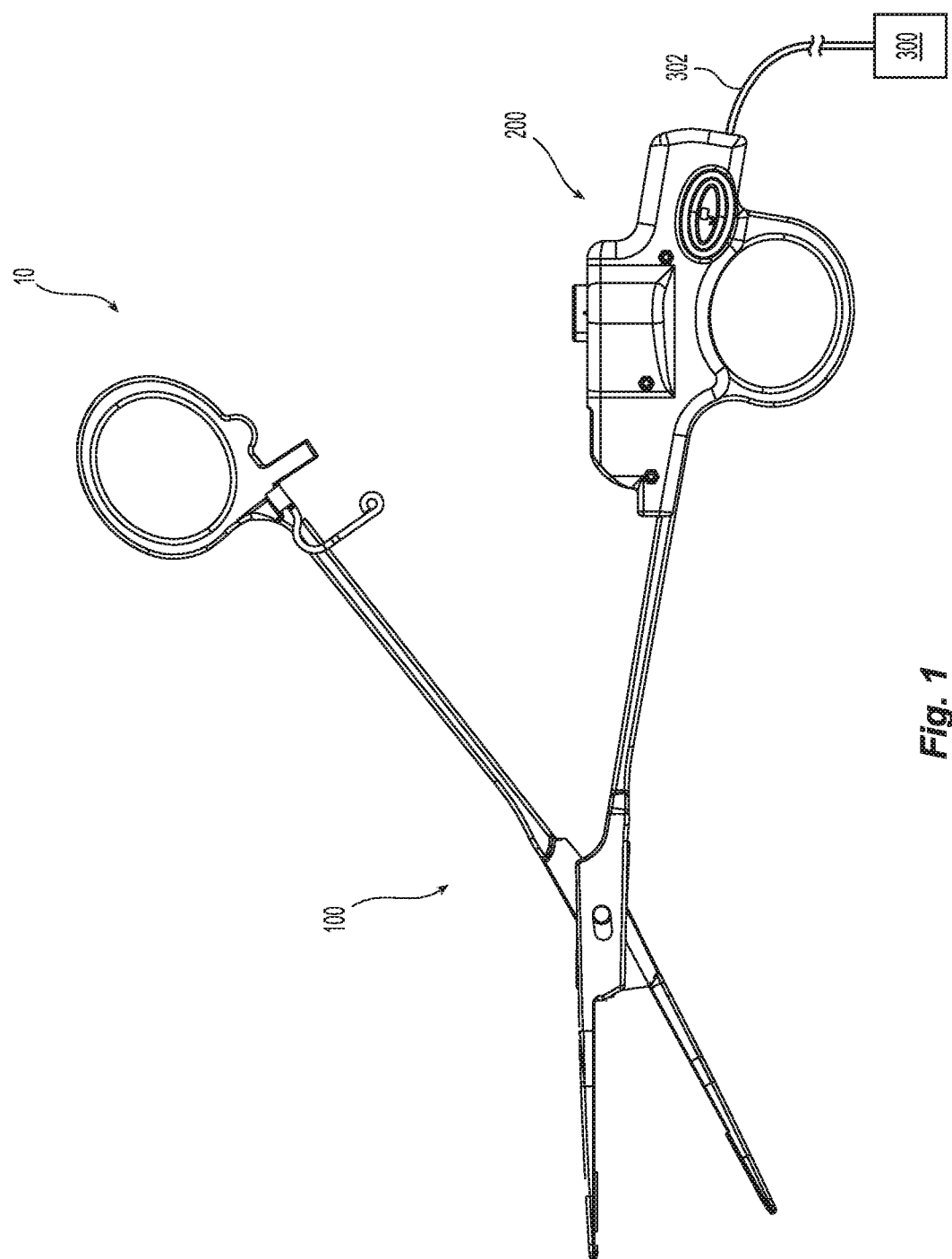
FIG. 1 is a side view of a surgical system including an open, assembled electrosurgical forceps having a handle connector assembly connected to a source of electrosurgical energy in accordance with an embodiment of the present disclosure.

In this disclosure, the term "proximal" refers to a portion of a structure closer to an operator, while the term "distal" refers to a portion of the same structure further from the operator. As used herein, the term "subject" refers to a human patient or animal. The term "operator" refers to a doctor (e.g., a surgeon), a nurse, and other clinicians or care providers, and may include support personnel.

Referring now to FIGS. 1-4, an energy-based surgical system 10 in accordance with the present disclosure is configured for grasping, electrically treating, and mechanically dissecting tissue or vessels in open and/or laparoscopic surgical procedures. The energy-based system 10 includes a reusable forceps 100 having a handle connector assembly 200 that is disposable and removably attachable to the forceps 100 and releasably connected to a source of electrosurgical energy 300 via cable 302. Alternatively, the handle connector assembly 200 may be reusable.

The forceps 100 include first and second elongated shaft members 110 and 120. The first elongated shaft member 110 includes proximal and distal end portions 112 and 114, respectively, and the second elongated shaft member 120 includes proximal and distal end portions 122 and 124, respectively. The proximal end portions 112 and 122 of the first and second shaft members 110 and 120 are first and second handle members 130 and 140, respectively. The first and second handle members 130 and 140 are configured to allow an operator to effect movement of at least one of the first and second shaft members 110 and 120 relative to the other. The distal end portions 114 and 124 of the first and second shaft members 110 and 120 cooperate to define an end effector assembly 115 having opposed first and second jaw members 150 and 160.

The first and second handle members 130 and 140 each define a finger hole 130a and 140a, respectively, therethrough for receiving a finger of an operator. The finger holes 130a and 140a facilitate movement of the first and handle members 130 and 140 relative to each other. The first and second handle members 130 and 140 are each monolithically formed with respective shaft members 110 and 120. Alternatively, the first and second handle members 130 and 140 may each be engaged with respective shaft members 110 and 120 in any suitable configuration, e.g., via mechanical engagement, molding, adhesion, etc.

The first handle member 130 includes a bump stopper 132, a connector pin 134, and a spring connector 136, each of which extends from an inner surface 130b of the first handle member 130 toward the second handle member 140. The bump stopper 132 includes an undulating shape or convex contour on the inner surface 130b of the first handle member 130. The connector pin 134 and the spring connector 136 each includes an elongated body 134a and 136a, respectively, that extends toward the second handle member 140 in a generally vertically aligned manner. The elongated body 136a of the spring connector 136 is disposed between a first end 136b that is secured to the first handle member 130 and a second end 136c defining an opening 136d for receiving a pin 136e securely therethrough.

The second handle member 140 includes an inner surface 140b including a raised rail 142 configured to matingly engage the handle connector assembly 200 to facilitate longitudinal alignment of the handle connector assembly 200 with respect to the second handle member 140. The raised rail 142 includes a recess 142a defined therein that is configured to receive a locking plate of the handle connector assembly 200 for securing the handle connector assembly 200 to the second handle member 140. The inner surface 140b of the second handle member 140 also includes a pair of raised projections 144 disposed on a distal end 140c of the second handle member 140 that are configured to be received within notches of the handle connector assembly 200 and to stop distal movement of the handle connector assembly 200 with respect to the second handle member 140.

With reference now to FIGS. 5-8, in conjunction with FIGS. 1-4, the first shaft member 110 intersects the second shaft member 120 at intersection portions 116 and 126 of the first and second shaft members 110 and 120, respectively. The intersection portion 116 of the first shaft member 110 includes a substantially flat body portion 116a including a pivot pin 116b extending transversely therethrough. Pivot pin 116b may be integrally formed with the body portion 116a or secured in an opening defined in the body portion 116a. A first face 116c of the body portion 116a includes a v-shaped recess 116d configured to receive a protrusion 126g extending from the intersection portion 126 of the second shaft member 120 to limit movement of the second shaft member 120 with respect to the first shaft member 110.

The second shaft member 120 includes a split body 126a including first and second legs 126b and 126c defining a slot 126d therebetween that is configured to receive the body portion 116a of the first shaft member 110. Such a configuration maintains central alignment of the first shaft member 110 with respect to the second shaft member 120, as well as minimizing jaw splay while sealing and cutting. The first and second legs 126b and 126c include diametrically opposed, and longitudinally aligned, oblong openings 126e and 126f, respectively, that are configured to receive the pivot pin 116b of the first shaft member 110. The pivot pin 116b is longitudinally slidable and pivotable within the oblong openings 126e and 126f. The first leg 126b includes a protrusion 126g on an inner surface thereof that engages the v-shaped recess 116d of the body portion 116a of the first shaft member 110. The protrusion 126g is free to move within an upper portion of the v-shaped recess 116d when the first and second jaw members 150 and 160 are in an approximated position (e.g., FIG. 7), and the pivot pin 116b is free to longitudinally move within the oblong openings 126e and 126f. The protrusion 126g is restricted within a lower portion of the v-shaped recess 116d when the jaw members 150 and 160 are in an open position (e.g., FIG. 8), and the pivot pin 116b is restricted to a proximal portion of the oblong openings 126e and 126f. The second leg 126c includes a removable plate 126h to facilitate assembly/disassembly of the first and second shaft members 110 and 120. Alternatively, plate 126h may be permanently secured to the second leg 126c or integrally formed with the second leg 126c.

The first and second shaft members 110 and 120 are coupled to one another at the pivot pin 116b and the oblong openings 126e and 126f such that movement of the first and second handle members 130 and 140 from an open, spaced apart position to one or more closed, approximated positions effects corresponding movement of the first and second jaw members 150 and 160 relative to one another. Accordingly, the first and second jaw members 150 and 160 are movable relative to each other in response to movement of the first and second handle members 130 and 140.

As shown in FIGS. 9-12, in conjunction with FIGS. 1-4, the first and second jaw members 150 and 160 extend distally from the intersection portions 116 and 126 of the first and second shaft members 110 and 120. Proximal portions 150a and 160a of the first and second jaw members 150 and 160 extend longitudinally from the intersection portions 116 and 126, and distal portions 150b and 160b of the first and second jaw members 150 and 160 curve away from the proximal portions 150a and 160a.

The first and second jaw members 150 and 160 include first and second tissue contacting surfaces 152 and 162 that are opposed to one another. The first and second tissue contacting surfaces 152 and 162 of the first and second jaw members 150 and 160 define complementary stepped surfaces which together seals and/or cuts tissue disposed therebetween. The first tissue contacting surface 152 includes a lower, base surface 152a and an upper, raised surface 152b that are laterally disposed relative to each other. An intermediate wall 152c extends perpendicular to, and connects, the base and raised surfaces 152a and 152b. A shear edge 152d is formed at the intersection of the raised surface 152b and the intermediate wall 152c. In some embodiments, the distal portions 150b and 160b of the first and second jaw members 150 and 160 include the complementary stepped tissue contacting surfaces and the proximal portions 150a and 160a of the first and second jaw members 150 and 160 include only the base surfaces 152a and 162a. It should be understood, however, that the complementary stepped tissue contacting surfaces can extend along any portion of the first and second jaw members 150 and 160.

Similarly, as described above with respect to the first tissue contacting surface 152, the second tissue contacting surface 162 includes a lower base surface 162a laterally disposed relative to an upper, raised surface 162b, and an intermediate wall 162c extending between and connecting the base and raised surfaces 162a and 162b. A shear edge 162d is disposed at the intersection of the raised surface 162b and the intermediate wall 162c.

Complementary guide surfaces 154 and 164 are defined at a distalmost end of each of the first and second jaw members 150 and 160 to reduce friction between the first and second jaw members 150 and 160 and facilitate longitudinal sliding of the first and second jaw members 150 and 160 with respect to one another. In some embodiments, the complementary guide surfaces 154 and 164 extend from the raised surfaces 152b and 162b of the first and second tissue contacting surfaces 152 and 162 and are twisted across the base surfaces 152a and 162a at the distalmost end of the first and second jaw members 150 and 160.

The first and second jaw members 150 and 160 are movable between an open position, a first approximated sealing position, and a second approximated cutting position. In the open position, as shown for example in FIG. 9, the first and second tissue contacting surfaces 152 and 162 are spaced apart from each other. In the first approximated position, as shown for example in FIG. 11, the first and second tissue contacting surfaces 152 and 162 are approximated and diametrically opposed to one another such that the base surface 152a of the first jaw member 150 is aligned with the raised surface 162b of the second jaw member 160 and the raised surface 152b of the first jaw member 150 is aligned with the base surface 162a of the second jaw member 160. In the second approximated position, as shown for example in FIG. 12, the first and second tissue contacting surfaces 152 and 162 are laterally offset from one another such that the raised surfaces 152b and 162b of the first and second jaw members 150 and 160 are aligned with each other.

The forceps 100 is formed of a conductive material, such as a metal, and includes an electrically insulative coating disposed over the forceps 100, except at the tissue contacting surfaces 152 and 162 of the first and second jaw members 150 and 160, the connector pin 134 of the first handle member 130, and at least a portion of the raised rail 142 of the second handle member 140. Accordingly, the tissue contacting surfaces 152 and 162, the connector pin 134, and a portion of the raised rail 142 are not coated with an electrically insulative material.

Figure 13:
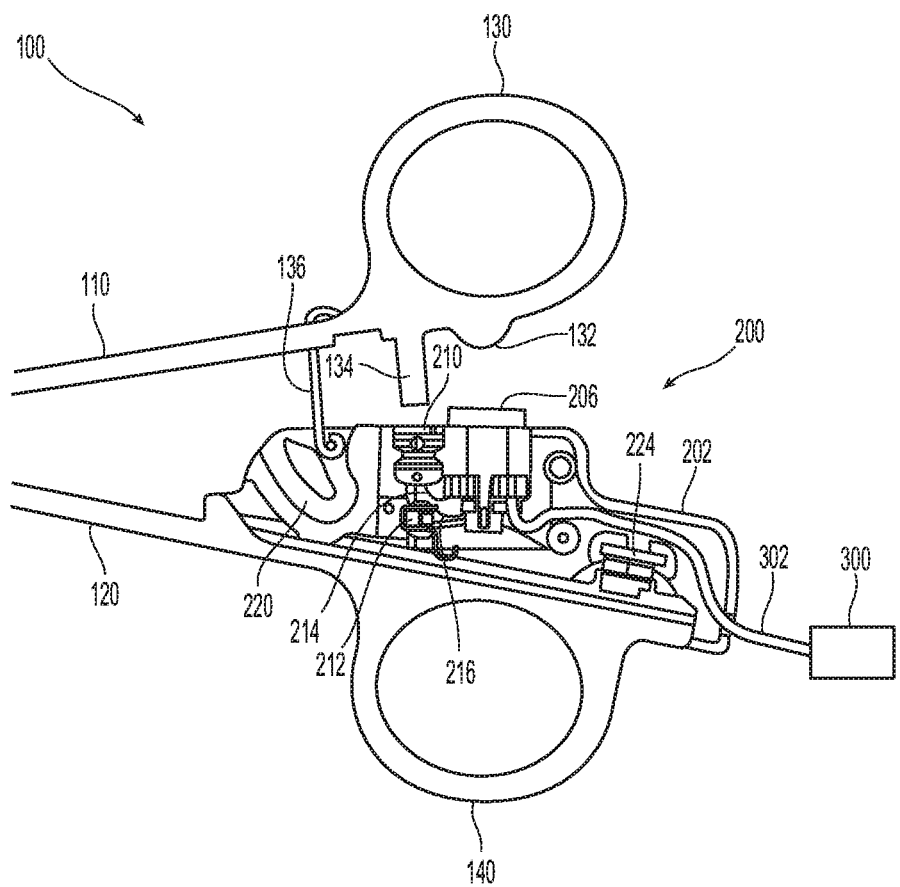
FIG. 13 is a side view of a portion of the forceps of FIG. 1, with the handle connector assembly shown in cross-section.
Figure 15:
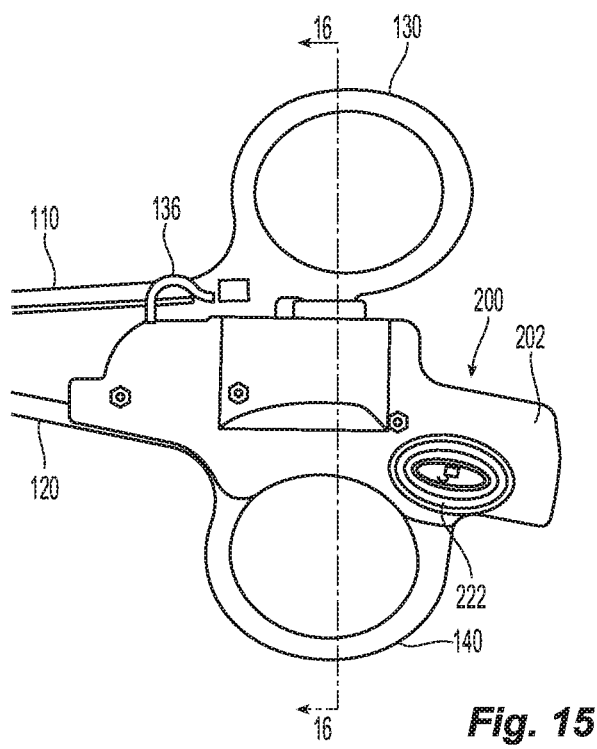
FIG. 15 is a side view of the handle connector assembly of FIG. 14.
Figure 16:
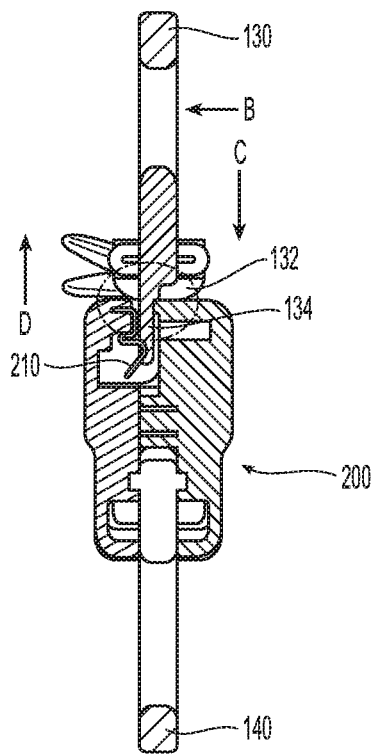
FIG. 16 is a rear, cross-sectional view of the surgical instrument of FIG. 15 take along line 16-16 of FIG. 15.

Referring now to FIG. 13, in conjunction with FIGS. 1-4, the handle connector assembly 200 includes a housing 202 including a lower surface 202a configured to engage the raised rail 142 of the second handle member 140. The lower surface 202a may be contoured for ergonomic fit with a finger of an operator positioned through the finger hole 140a of the second handle member 140. The housing 202 includes a distal end 202b including notches 204 configured to receive the raised projections 144 of the second handle member 140. The housing 202 includes an upper surface 202c including a switch or power button 206 disposed in general alignment with the bump stopper 132 of the first handle member 130. The upper surface 202c defines an opening 208 including a proximal portion 208a in general alignment with the connector pin 134 of the first handle member 130, an intermediate portion 208b laterally offset from the proximal portion 208a, and a distal portion 208c through which the spring connector 136 of the first handle member 130 may travel.

First and second conductive connector members 210 and 212 are disposed within the housing 202 and laterally spaced from each other. Cables 214 and 216 connect the first and second connector members 210 and 212 to the power button 206, respectively, and a cable 302 extends from the power button 206 and out through a proximal end 202d (FIG. 2) of the housing 202 for electrically connecting the forceps 100 to an electrosurgical energy source 300, such as an RF generator. A portion of the first connector member 210 is in general alignment with the proximal portion 208a (FIG. 4) of the opening 208 defined in the upper surface 202c of the housing 202. The second connector member 212 is in contact with the portion of the raised rail 142 that does not include the electrically insulative coating. The first connector member 210 is movable into contact with the second connector member 212 in response to movement of the connector pin 134 of the first handle member 130 into the housing 202. A generally u-shaped channel 220 forms a path in and out of the distal portion 208c (FIG. 4) of the opening 208 through which the pin 136c of the spring connector 136 travels. A user control button 222 (FIG. 2) is disposed through the housing 202 and is mechanical engagement with a locking plate 224 disposed within the housing 202 to actuate the locking plate 224 in and out of engagement with the recess 142a defined within the raised rail 142 of the second handle member 140 to lock and release the handle connector assembly 200 to and from the forceps 100.

Figure 2:
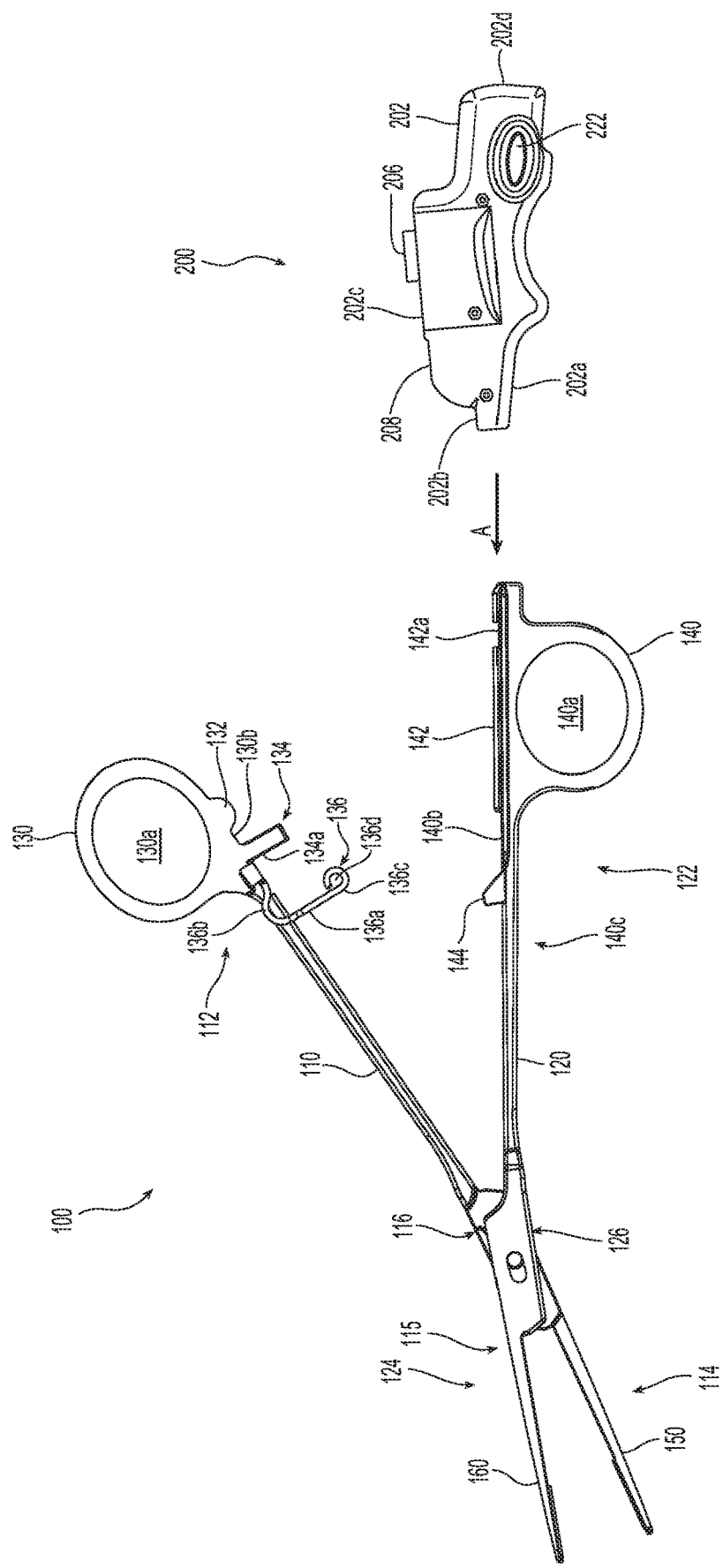
FIG. 2 is a side view of the forceps of FIG. 1 in a disassembled state in accordance with the present disclosure.
Figure 3:
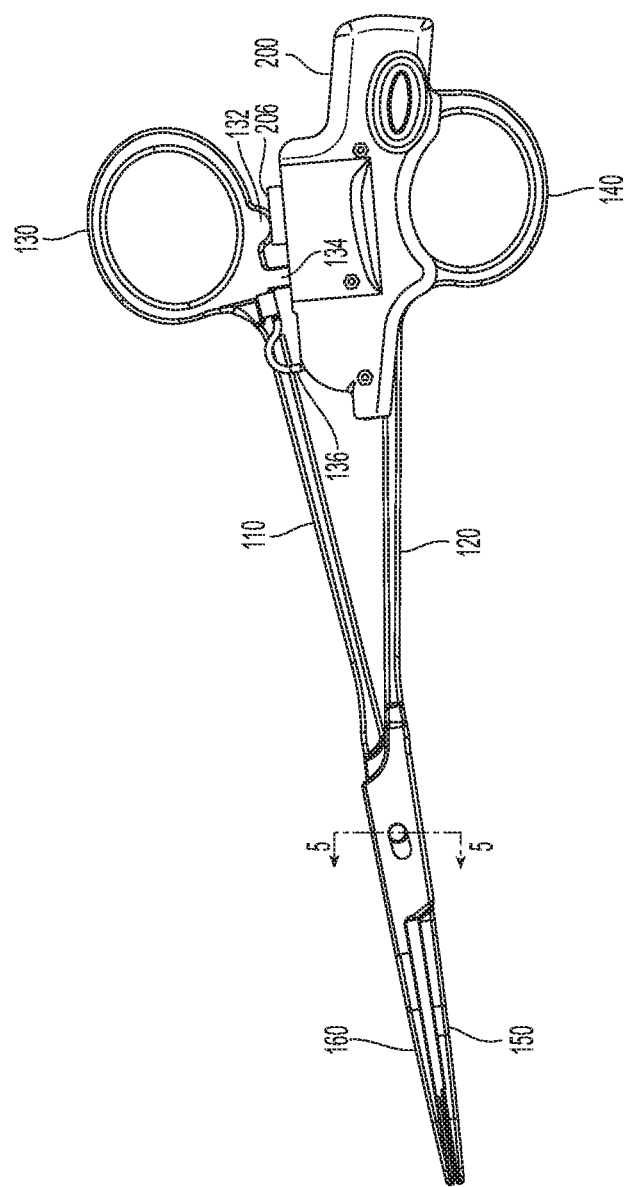
FIG. 3 is a side view of the forceps of FIG. 1 in a first approximated position.
Figure 4:
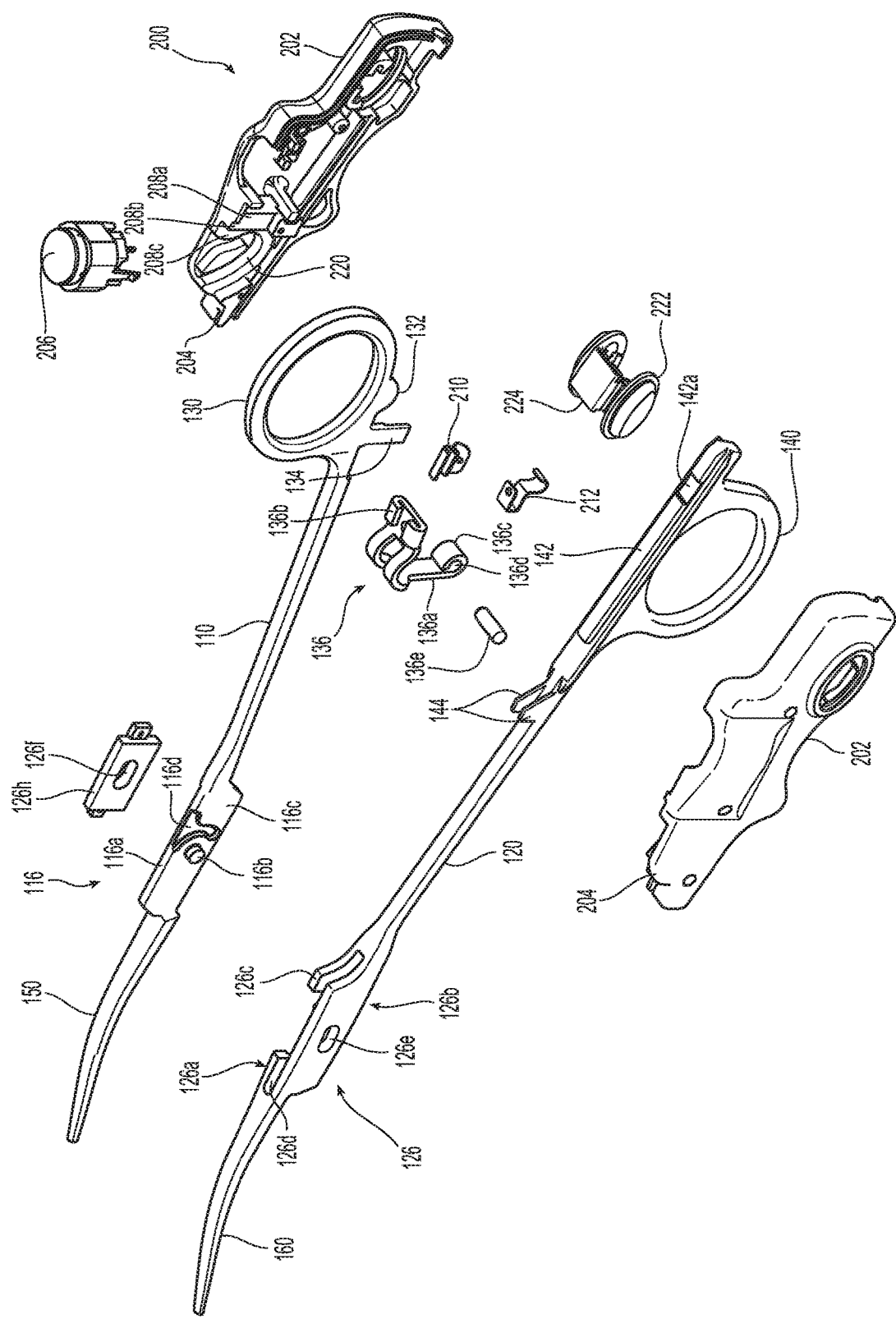
FIG. 4 is a perspective view of the forceps of FIG. 1 with parts separated.
Figure 5:
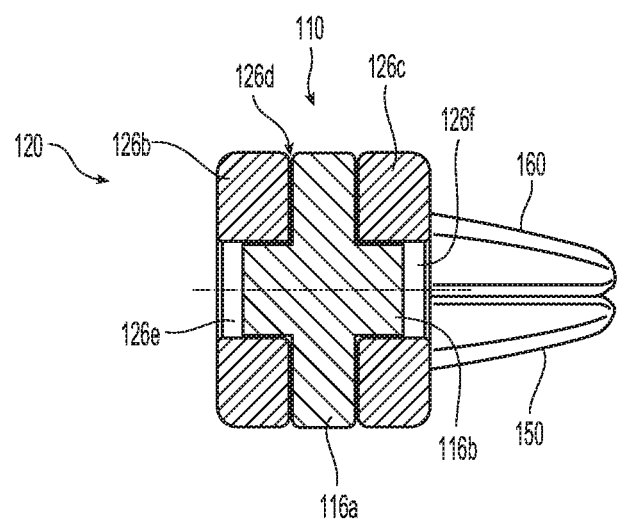
FIG. 5 is a cross-sectional view of the forceps of FIG. 3 taken along line 5-5 of FIG. 3.
Figure 6:
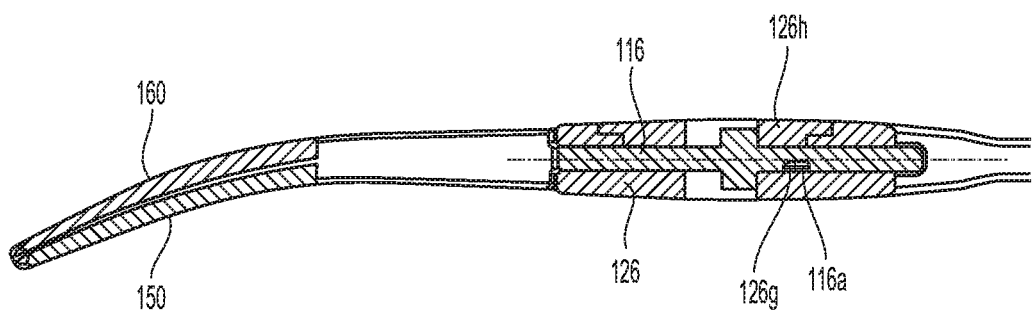
FIG. 6 is a bottom, cross-sectional view of a portion of the forceps of FIG. 3.
Figure 7:
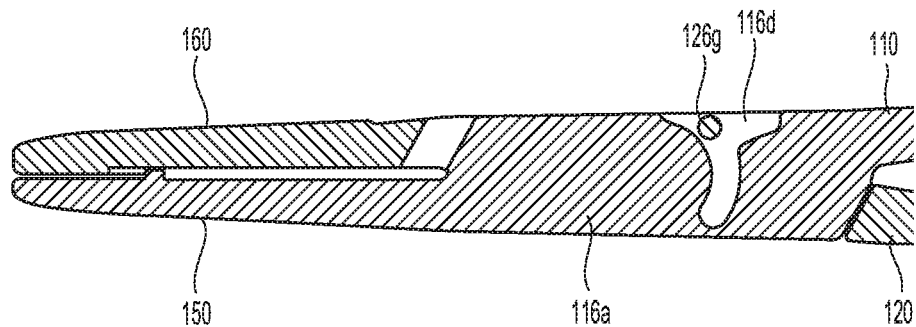
FIG. 7 is a side, cross-sectional view of a portion of the forceps of FIG. 3.
Figure 8:
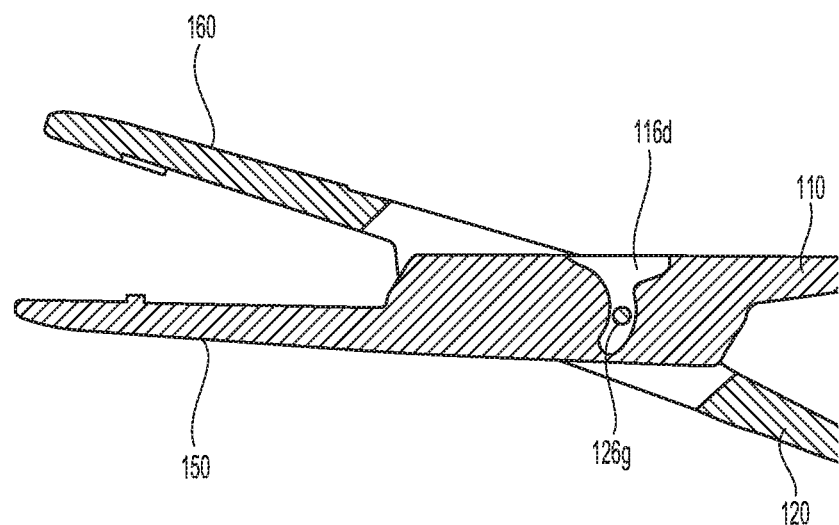
FIG. 8 is a side, cross-sectional view of a portion of the forceps of FIG. 1.
Figure 9:
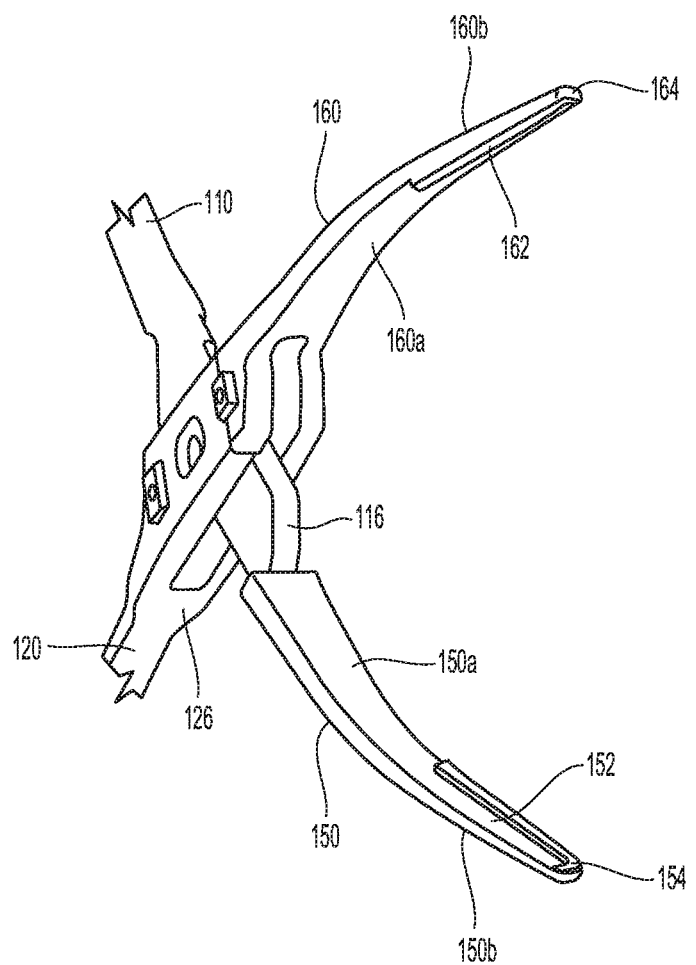
FIG. 9 is a side, perspective view of a distal portion of the forceps of FIG. 1.
Figure 10:
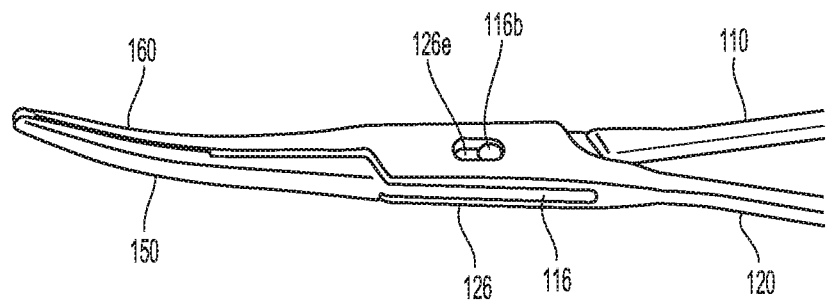
FIG. 10 is a bottom, perspective view of a portion of the forceps of FIG. 3.
Figure 11:
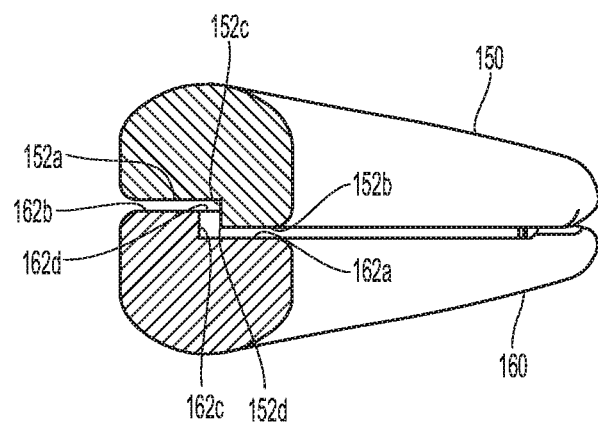
FIG. 11 is a perspective view, in partial cross-section, of first and second jaw members of the forceps of FIG. 3.
Figure 12:
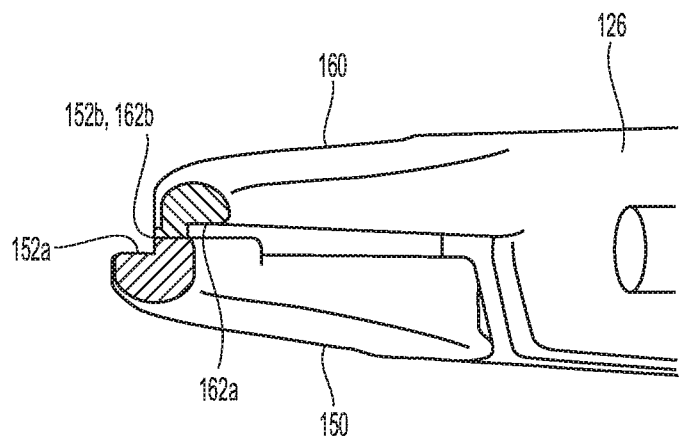
FIG. 12 is a side, perspective view, in partial cross-section, of first and second jaw members of the forceps of FIG. 3 in a second approximated position.

In an example method of assembling the forceps 100, as shown in FIGS. 1-3, the lower surface 202a of the housing 202 of the handle connector assembly 200 is aligned with the raised rail 142 of the second handle member 140 when the forceps 100 are in an open position. The housing 202 is slid distally in the direction of arrow "A" (FIG. 2), along the raised rail 142 until the notches 204 (FIG. 4) defined within the distal end 202b of the housing 202 engage the protrusions 144 formed at the distal end of the second handle member 140. The user control button 222 is then depressed to move the locking plate 224 into engagement with the recess 142a defined in the raised rail 142 of the second handle member 140 to secure the handle connector assembly 200 to the forceps 100.

In an example method of using the assembled forceps 100, the forceps 100 is placed at a desired surgical site and the first and second jaw members 150 and 160 are positioned in an open position around desired tissue and/or vessel(s). The first and second handle members 130 and 140 are approximated by moving at least one of the first and second handle members 130 and 140 towards the other such that the first and second handle members 130 and 140 pivots with respect to the other about the pivot pin 116b in the proximal portion of the oblong openings 126e and 126f. When the first and second handle members 130 and 140 are brought together in this first, approximated position, as shown in FIG. 14, the bump stopper 132 depresses the power button 206 while the connector pin 134 enters the housing 202 through the proximal portion 208a (FIG. 4) of the opening 208 defined in the upper surface 202c of the housing 202 and contacts the first connector member 210, which in turn contacts the second connector member 212 to close the electrical circuit and energize the tissue contacting surfaces 152 and 162 of the first and second jaw members 150 and 160 to seal tissue "T" disposed therebetween. At the same time, the spring connector 136 enters the distal portion 208c (FIG. 4) of the opening 208 defined in the upper surface 202c of the housing 202 and moves into a proximal portion of the u-shaped channel 220. Sealing is effected, for example, by the application of pressure on the tissue "T" between the first and second jaw members 150 and 160, and the electrosurgical energy transferred from the electrosurgical energy source. In some embodiments, the minimum seal width is equal to or greater than 0.46 mm. In some embodiments, the closure pressure between the first and second jaw members 150 and 160 for sealing tissue is in the range of about 3 kg/cm$^2$ to about 16 kg/cm$^2$. In some embodiments, a gap distance between the first and second jaw members 150 and 160 during sealing is in the range of about 0.001 inches to about 0.006 inches.

Figure 17A:
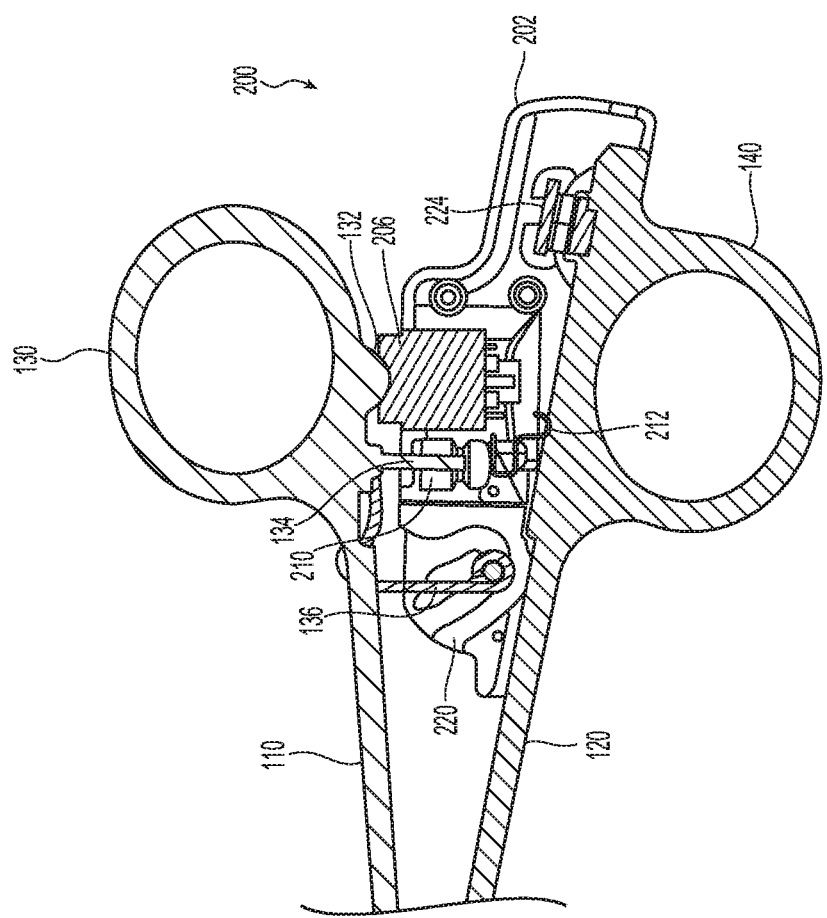
FIG. 17A is a side view, in partial cross-section, of a portion of the forceps of FIG. 14 in a transition position between the first and second approximated positions.
Figure 17B:
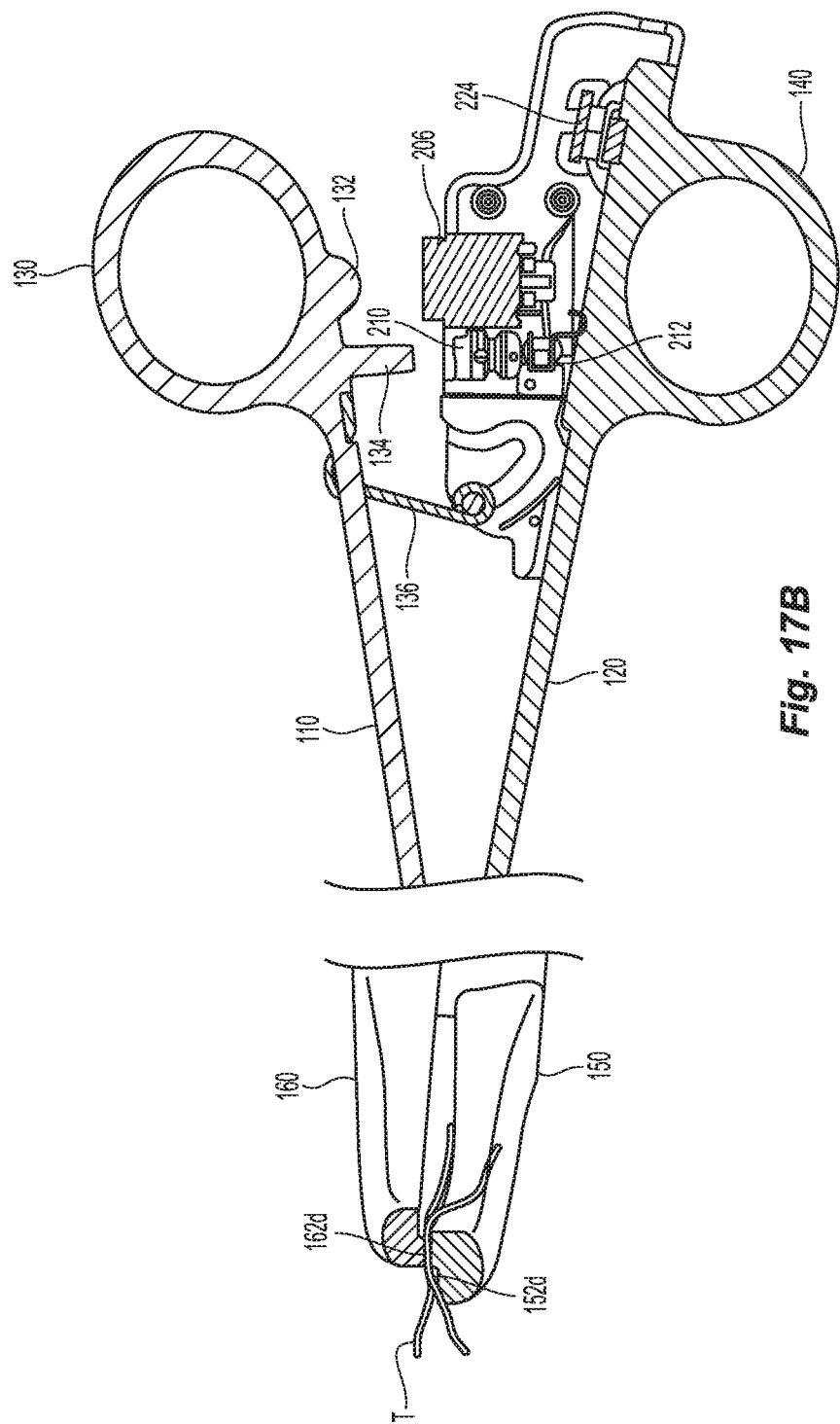
FIG. 17B is a side, perspective view, in partial cross-section, of the forceps of FIG. 17A in a second approximated position.

When sealing is complete, the first and second handle members 130 and 140 may be returned to the open position to release the tissue "T" or may be moved to a second, approximated position to cut the tissue "T" disposed between the first and second jaw members 150 and 160. As shown in FIGS. 15-17B, to move to the second approximated position, the first handle member 130 is moved laterally, in the direction of arrow "B" and pushed down in the direction of arrow "C" such that the connector pin 134 enters the intermediate portion 208b (FIG. 4) of the opening 208 defined in the upper surface 202c of the housing 202. At the same time, the bump stopper 132 releases the power button 206 and the spring connector 136 is initially moved into a distal portion of the u-shaped channel 220 (FIG. 17A). The first handle member 130 is then pulled up in the direction of arrow "D" such that the spring connector 136 is moved through the distal portion of the u-shaped channel 220 (FIG. 17B). This movement of the first handle member 130 causes the pivot pin 116b (FIG. 4) to longitudinally translate within the oblong openings 126e and 126f of the first and second jaw members 150 and 160 to cut the tissue "T" held therebetween. Cutting is effected, for example, by the application of pressure on the tissue "T" between the first and second jaw members 150 and 160, and longitudinal movement of the shear edges 152d and 162d of the first and second tissue contacting surfaces 152 and 162 with respect to each other.

To disassemble the handle connector housing 200 from the forceps 100, the operator presses the user control button 222 and pulls the handle connector assembly 200 proximally away from the second handle member 140. The forceps 100 may then be sterilized and reused with the same or different handle connector assembly 200. In some embodiments, the forceps 100 may be disassembled such that the first and second shaft members 110 and 120 are separated from each other by removing the plate 126h from the second leg 126c of the second shaft member 120.

The embodiments disclosed herein may also be configured to work with robotic surgical systems and what is commonly referred to as "Telesurgery." Such systems employ various robotic elements to assist the operator and allow remote operation (or partial remote operation) of surgical instrumentation. Various robotic arms, gears, cams, pulleys, electric and mechanical motors, etc. may be employed for this purpose and may be designed with a robotic surgical system to assist the operator during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep a subject (e.g., a patient) for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 18:
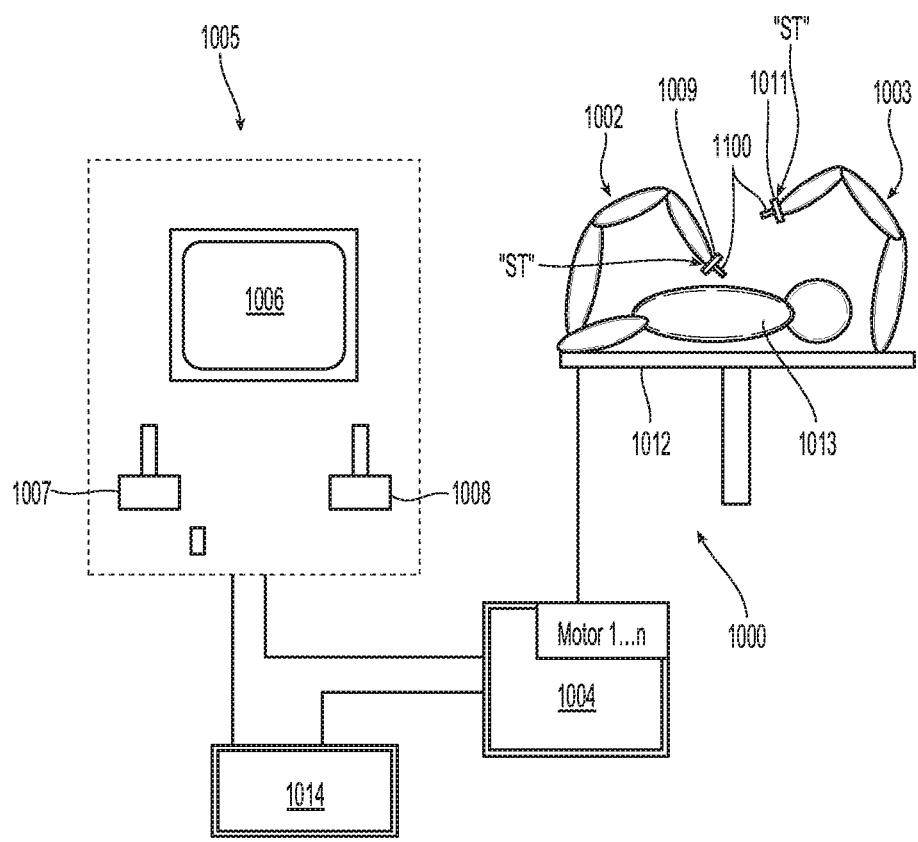
FIG. 18 is a schematic illustration of a work station configured for use with a forceps of the present disclosure.

Referring now to FIG. 18, a medical work station is shown generally as work station 1000 and generally may include a plurality of robot arms 1002 and 1003; a control device 1004; and an operating console 1005 coupled with control device 1004. Operating console 1005 may include a display device 1006, which may be set up in particular to display three-dimensional images; and manual input devices 1007 and 1008, by means of which an operator (not shown), for example a surgeon, may be able to telemanipulate robot arms 1002 and 1003 in a first operating mode.

Each of the robot arms 1002 and 1003 may include a plurality of members, which are connected through joints, and an attaching device 1009 and 1011, to which may be attached, for example, a surgical tool "ST" supporting an end effector 1100, in accordance with any one of several embodiments disclosed herein, as will be described in greater detail below.

Robot arms 1002 and 1003 may be driven by electric drives (not shown) that are connected to control device 1004. Control device 1004 (e.g., a computer) may be set up to activate the drives, in particular by means of a computer program, in such a way that robot arms 1002 and 1003, their attaching devices 1009 and 1011 and thus the surgical tool (including end effector 1100) execute a desired movement according to a movement defined by means of manual input devices 1007 and 1008. Control device 1004 may also be set up in such a way that it regulates the movement of robot arms 1002 and 1003, and/or of the drives.

Medical work station 1000 may be configured for use on a patient 1013 lying on a patient table 1012 to be treated in a minimally invasive manner by means of end effector 1100. Medical work station 1000 may also include more than two robot arms 1002 and 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to control device 1004, in which are stored, for example, pre-operative data from patient/living being 1013 and/or anatomical atlases.

While several embodiments of the disclosure have been shown in the drawings and described herein, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. An electrosurgical forceps, comprising:
a first elongated shaft member including a proximal end portion having a first handle member and a distal end portion including a first jaw member having a first tissue contacting surface;
a second elongated shaft member including a proximal end having a second handle member and a distal end portion including a second jaw member having a second tissue contacting surface;
at least one of the first or second handle members movable relative to the other between an open position, a first approximated position where the first and second tissue contacting surfaces are diametrically opposed to one other, and a second approximated position where the first and second tissue contacting surfaces are laterally offset from one other; and
a handle connector assembly including a housing selectively engageable with an inner surface of the second handle member, the handle connector assembly configured to communicate electrosurgical energy between the first and second tissue contacting surfaces when the first and second handle members are disposed in the first approximated position,
wherein the first handle member includes a connector pin extending towards the second handle member, the connector pin being spaced from the handle connector assembly when the first and second handle members are disposed in the open position, the connector pin configured to extend through a proximal portion of an opening defined in the housing and into contact with a movable first connector member disposed within the housing to close an electrical circuit when the first and second handle members move to the first approximated position, and
wherein the connector pin is disposed in an intermediate portion of the opening in the housing, which is distal to, and laterally offset from, the proximal portion of the opening, when the first and second handle members are moved to the second approximated position.

2. The forceps according to claim 1, wherein the first handle member includes a bump stopper disposed on an inner surface of the first handle member and extending towards the second handle member, wherein the bump stopper is spaced from the handle connector assembly when the first and second handle members are disposed in the open position, the bump stopper configured to engage a switch disposed on the housing of the handle connector assembly when the first and second handle members move to the first approximated position.

3. The forceps according to claim 1, wherein the first handle member includes a spring connector extending towards the second handle member, wherein the spring connector is spaced from the handle connector assembly when the first and second handle members are disposed in the open position, the spring connector configured to extend through the opening defined in the housing and into a proximal portion of a channel disposed within the housing when the first and second handle members are moved to the first approximated position.

4. The forceps according to claim 3, wherein the spring connector is disposed within a distal portion of the channel disposed within the housing of the handle connector assembly when the first and second handle members are moved to the second approximated position.

5. The forceps according to claim 1, wherein the first shaft member includes a body portion including a pivot pin and the second shaft member includes a split body portion including first and second legs defining opposed oblong openings, wherein the body portion of the first shaft member is disposed within a slot defined between the first and second legs of the split body portion and the pivot pin extends into the oblong openings.

6. The forceps according to claim 5, wherein when the first and second handle members are in the first approximated position, the pivot pin is disposed in a proximal portion of the oblong openings.

7. The forceps according to claim 6, wherein when the first and second handle members are in the second approximated position, the pivot pin is disposed in a distal portion of the oblong openings.

8. The forceps according to claim 1, wherein the first and second tissue contacting surfaces define complementary stepped surfaces.

9. The forceps according to claim 8, wherein the first and second tissue contacting surfaces each include a base surface laterally disposed relative to a raised surface, the base and raised surfaces connected by an intermediate wall that forms a shear edge at an intersection with the raised surface.

10. The forceps according to claim 9, wherein when the first and second handle members are in the first approximated position, the base and raised surfaces of the first tissue contacting surface are aligned with the raised and base surfaces of the second tissue contacting surface, respectively, and when the first and second handle members are disposed in the second approximated position, the raised surfaces of the first and second tissue contacting surfaces are aligned with each other.

11. An electrosurgical forceps, comprising:
a first elongated shaft member including a proximal end portion having a first handle member including a spring connector and a distal end portion including a first jaw member having a first tissue contacting surface;
a second elongated shaft member including a proximal end having a second handle member and a distal end portion including a second jaw member having a second tissue contacting surface;
at least one of the first or second handle members movable relative to the other between an open position, a first approximated position where the first and second tissue contacting surfaces are diametrically opposed to one other, and a second approximated position where the first and second tissue contacting surfaces are laterally offset from one other; and
a handle connector assembly including a housing removably attachable to the second handle member, the handle connector assembly configured to communicate electrosurgical energy between the first and second tissue contacting surfaces when the first and second handle members are disposed in the first approximated position, the housing including a U-shaped channel defined therein configured to receive the spring connector of the first handle member, the spring connector configured to ride within the U-shaped channel upon approximation of the first and second handle members.

12. The forceps according to claim 11, wherein the spring connector includes an elongated body extending towards the second handle member in vertical registration with a proximal portion of the U-shaped channel.

13. The forceps according to claim 12, wherein the elongated body of the spring connector includes a first end secured to the first handle member and a second end defining an opening for receiving a pin securely therethrough.

14. The forceps according to claim 11, wherein the spring connector is spaced from the handle connector assembly when the first and second handle members are disposed in the open position and the spring connector moves through a proximal portion of the U-shaped channel of the housing when the first and second handle members are moved from the open position to the first approximated position.

15. The forceps according to claim 14, wherein the spring connector moves through a distal portion of the U-shaped channel of the housing when the first and second handle members are moved from the first approximated position to the second approximated position.

16. An electrosurgical forceps, comprising:
a first elongated shaft member including a proximal end portion having a first handle member and a distal end portion including a first jaw member having a first tissue contacting surface;
a second elongated shaft member including a proximal end having a second handle member and a distal end portion including a second jaw member having a second tissue contacting surface;
at least one of the first or second handle members movable relative to the other between an open position, a first approximated position where the first and second tissue contacting surfaces are diametrically opposed to one other, and a second approximated position where the first and second tissue contacting surfaces are laterally offset from one other; and
a handle connector assembly including a housing selectively engageable with an inner surface of the second handle member, the handle connector assembly configured to communicate electrosurgical energy between the first and second tissue contacting surfaces when the first and second handle members are disposed in the first approximated position, wherein the first handle member includes a spring connector extending towards the second handle member, the spring connector spaced from the handle connector assembly when the first and second handle members are disposed in the open position, the spring connector configured to extend through an opening defined in the housing and into a proximal portion of a channel disposed within the housing when the first and second handle members are moved to the first approximated position, and wherein the spring connector is disposed within a distal portion of the channel disposed within the housing of the handle connector assembly when the first and second handle members are moved to the second approximated position.

* * * * *